United States Patent

Danielzik et al.

[11] Patent Number: 5,822,472
[45] Date of Patent: Oct. 13, 1998

[54] PROCESS FOR DETECTING EVANESCENTLY EXCITED LUMINESCENCE

[75] Inventors: Burkhard Danielzik, Ingelheim; Gert Ludwig Duveneck, Krozingen; Martin Heming, Stromberg, all of Germany; Dieter Neuschäfer, Muttenz, Switzerland; Johannes Segner, Stromberg, Germany

[73] Assignee: Novartis Corporation, Summit, N.J.

[21] Appl. No.: 737,846

[22] PCT Filed: May 17, 1995

[86] PCT No.: PCT/IB95/00368

§ 371 Date: Mar. 4, 1997

§ 102(e) Date: Mar. 4, 1997

[87] PCT Pub. No.: WO95/33198

PCT Pub. Date: Dec. 7, 1995

[30] Foreign Application Priority Data

May 27, 1994 [CH] Switzerland ............... 1643/94

[51] Int. Cl.⁶ .................................................. G02B 6/10
[52] U.S. Cl. ......................... 385/12; 385/37; 385/130; 385/131
[58] Field of Search ......................... 250/458.1, 459.1; 385/12, 129, 130, 131, 37, 147

[56] References Cited

U.S. PATENT DOCUMENTS 5,082,629  1/1992  Burgess, Jr. et al. .................. 385/12

FOREIGN PATENT DOCUMENTS 8909394  10/1989  WIPO .
9006503   6/1990  WIPO .
9110122   7/1991  WIPO .

Primary Examiner—John Ngo
Attorney, Agent, or Firm—George R. Dohmann

[57] ABSTRACT

The invention relates to a process for determing lumnescence with a planar dielectric optical sensor platform which consists of a transparent substrate to which a thin transparent waveguiding layer is applied, which sensor platform is provided with a coupling grating for the input-coupling of the excitation light and the refractive index of the substrate is lower than the refractive index of the waveguiding layer, by briging a liquid sample as superstrate into contact with the layer, and measuring the luminescence produced by substances having luminescence properties in the sample, or by substances having luminescence properties immobilized on the layer, optoelectronically. The invention also relates to the use of the process in quantitative affinity sensing and to the use thereof for the quantitative determination of luminescent constituents in optically turbid solutions, and to sensor platform for carrying out the process.

36 Claims, 2 Drawing Sheets

PROCESS FOR DETECTING EVANESCENTLY EXCITED LUMINESCENCE

The present invention relates to a process for detecting evanescently excited luminescence with a planar dielectric optical sensor platform based on a waveguide. The invention also relates to the use of said process in qualitative affinity sensing and to the use thereof for the selective quantitative determination of luminescent components in optically turbid solutions. The invention further relates to a sensor platform suitable for carrying out the process.

Where light propagates in a waveguide, the lightwave is not completely limited to the actual waveguide: in fact a fraction of the lightwave propagates in the contiguous optically thinner medium. This fraction is termed the evanescent field and is the basis of the variegated use of optical waveguides in sensing technology.

With the evanescent field it is possible in particular to excite luminescence in the optically thinner medium. This excitation is limited to the immediate environment of the interface of the waveguide. Evanescent luminescence excitation is therefore of great interest for analytical purposes.

A planar sensor consists in the simplest case of a 3-layer system: a substrate, a waveconducting layer, and a superstrate that usually constitutes the sample for assaying. Especially in the case of thin waveguides in which the thickness of the waveguiding layer is smaller than the light wave length, the number of diffusible modes of the light field capable of propagation is limited to a few discrete waveguide modes.

In the case of thick waveguides, a host of modes can be guided. In this case the need for a substrate can often be dispensed with, for example for thicknesses in the range of several $\frac{1}{10}$ mm and greater.

Prior art methods of detecting evanescently excited luminescence can be differentiated in accordance with the choice of radiation fractions that can be detected:

Detection of the "volume luminescence": a fraction of the fluorescence excited by the guided wave is emitted into the full space angle; this fraction can be optically recorded and fed into a detection system.

Detection of the "evanescent luminescence": complementary to the luminescence emitted into the space, this evanescent luminescence is back-coupled as guided wave into the waveguide, transported there and coupled out via the end plane of the waveguide.

Methods and apparatus for detecting the evanescently excited luminescence of antibodies or antigens labelled with luminescent dyes are known and described, inter alia, in U.S. Pat. No. 4,582,809. The arrangement claimed therein uses an optical fibre and endface coupling for the evanescent luminescence excitation. Such optical fibres typically have a diameter of up to 1 millimeter and conduct a host of modes when laser light is coupled thereinto. The evanescently excited luminescence can be measured in simple manner only by the fraction tunnelled back into the fibre. The quite large dimensions of the apparatus and the fact that comparatively large sampling volumes are required are further drawbacks. The apparatus cannot be substantially reduced in size or even miniaturised to integrated optical sensors. An enhancement of the sensitivity is usually associated with an increase in the size of the apparatus.

A further drawback is the sensitivity which is limited by the endface output-coupling: as excitation and luminescence radiation run co-linearly and have to be separated by beam splitters and filters (e.g. cut-off filters or band-pass filters), the discrimination characteristics of the filter unit limits the detection sensitivity.

The use of thick planar multimode waveguides is described by D. Christensen, D. Deyer, D. Fowers, J. Herron in "Analysis of Excitation and Collection Geometries for Planar Waveguide Immunosensors", SPIE 1886, 2(1993) (Fibre Optic Sensors in Medical Diagnostics). Here the excitation radiation is coupled into the waveguide via the endface, and the luminescence light emitted into the space angle is detected. Alternatively it is also possible to use an endface output-coupling. In this latter case, the limitation of sensitivity caused by the necessary beam splitters and filters are a drawback in the same way as in the arrangements described above. Further disadvantages here are also the large sensor dimensions and the large sample volumes associated therewith.

In WO 90/06503 there is disclosed a process for exciting luminescence by total internal reflection fluorescence (TIRF) using thin planar, preferably monomode, waveguides. The waveguide in this process is used to increase the light field strength at the sensor surface, the excitation radiation being beamed in from the underside and reflected totally at the sensor. The volume luminescence emitted into the space angle is detected. In this process, the interaction zone between excitation light and molecules having luminescent properties is limited on the sensor, as excitation takes place only in the area of the beam diameter. There are therefore only limited possibilities of dimensioning the sensor via the beam diameter, with restrictions in diameter and divergence owing to the very narrowly confined resonance angle.

The prior art use of one or more than one coupling grating for the input- or output-coupling of guided waves is described by K. Tiefenthaler and W. Lukosz in "Sensitivity of grating couplers as integrated-optical chemical sensors", J. Opt. Am. B6, 209 (1989), by W. Lukosz, Ph.M. Nellen, Ch. Stamm and P. Weiss, in "Output Grating Couplers on Planar Waveguides as Integrated Opitcl Chemical Sensors", Sensors and Actuators B1, 585 (1990), and by T. Tamir and S. T. Peng, in "Analysis and Design of Grating Couplers", Appl. Phys. 14, 235–254 (1977). The processes described by Tiefenthaler et al. are useful for affinity sensing by the direct detection method (via the change in refractive index). The displacement of the coupling angle resonance is determined which, owing to the change in refractive index, is governed by adsorption or binding of molecules.

Various attempts have been made to enhance the sensitivity of evanescently excited luminescence and to fabricate integrated optical sensors. Thus, for example, Biosensors & Bioelectronics 6 (1991), 595–607 reports on planar monomode or low-mode waveguides which are fabricated in a two-step ion exchange process and in which the coupling of light into the excitation wave is effected with prisms. The affinity system used is human immunoglobulinG/fluorescein-labelled proteinA, wherein the antibody is immobilised on the waveguide and the fluorescein-labelled proteinA to be detected, in phosphate buffer, is added to a film of polyvinyl alcohol with which the measuring region of the waveguide is coated. A substantial disadvantage of this process is that only minor differences in the refraction indices between waveguiding layer and substrate layer are achievable, resulting in a relatively low sensitivity.

The sensitivity is said to be 20 nm in fluorescein isothiocyanate bonded to proteinA. This is still unsatisfactory for being able to detect microtraces, and a further enhancement of sensitivity is necessary. Moreover, the reproducibility and practical viability of coupling light into the excitation wave by prisms seems difficult on account of the considerable dependence of the coupling efficiency on the quality and size of the contact area between prism and waveguide.

The use of gratings for the luminescence detection as claimed in this invention is described in U.S. Pat. No. 5,081,012. This U.S. patent discloses grating structures for coupling excitation light into a waveguide as well as special reflection gratings which enable the excitation wave to traverse the waveguide a number of times. Enhanced sensitivity is said to be achieved by this means. The volume luminescence emitted into the space angle. Moreover, the excitation radiation coupled out of the input-coupling grating after two traversals can be used as reference signal. The drawback of this process is the strong increase of the background radiation intensity caused by the reflection grating and which is emitted with the luminescence signal into the space angle. The characteristics of the necessary filters once again limit the detection sensitivity.

The invention has for its object to provide a process for determining luminescence with a planar optical waveguide, which process is simple and economically viable and for which, in particular, only small sample volumes are necessary. It is a further object of the invention to provide a miniaturisable sensor platform on the basis of a planar optical waveguide for carrying out the process.

This object is achieved with a process for determining luminescence with a planar dielectric optical sensor platform which consists of a transparent substrate (a) to which a thin transparent waveguiding layer (b) is applied, which sensor platform is provided with a coupling grating for the input-coupling of the excitation light and the refractive index of said substrate (a) is lower than the refractive index of the waveguiding layer (b), by bringing a liquid sample as superstrate into contact with the layer (b), and measuring the luminescence produced by substances having luminescence properties in the sample, or by substances having luminescence properties immobilised on the layer (b), optoelectronically, by coupling the excitation light with the coupling grating into the planar waveguide so that it traverses the waveguiding layer, whereby the substances having luminescence properties are excited to luminescence in the evanescent field of the waveguiding layer, which process comprises using a waveguiding layer having a thickness smaller than the wavelength λ of the excitation radiation and which consists of a material whose refractive index at the wavelength of the excitation radiation is ≧1.8, and coupling out from the waveguiding layer, and detecting, the luminescence radiation coupled back into the waveguiding layer (b) with a second coupling grating spatially separated from the first coupling grating.

Preferred utilities of the process form the subject matter of claims 20 to 23. A sensor platform and the preferred embodiments thereof which are particularly suitable for carrying out the process of the invention are described in claims 24 to 38. Preferred embodiments of the process form the subject matter of claims 2 to 19.

In the practice of this invention, the excitation radiation is coupled into the waveguide with a coupling grating and propagates in the waveguiding layer as guided wave. For the efficient evanescent excitation of the luminescence it is possible to achieve a high field strength at or near the sensor surface by choice of the wavelength parameters (refractive index, layer thickness).

Surprisingly, it has been found that, for the dimensioning of the waveguide described hereinbelow, a substantial fraction of the luminescence radiation is coupled back evanescently into the waveguide and is transported by the waveguide together with the excitation wave. Hence the luminescence radiation can be coupled out of the waveguide via a second coupling grating which is spatially separated from the first coupling grating and is conducted to the detection system. The advantage of this "grating detection evanescent luminescence" over the "volume detection" of the prior art resides in the simplified possibility of minitiaturising the sensor platform and the detection system pertaining thereto.

The dimensioning of planar waveguides for the most efficient luminescence excitation possible can be effected on the basis of the theory of planar waveguides. The following dimensions are in this connection to be observed (W. Lukosz "Principles and sensitivities of integrated optical and surface plasmon sensors for direct affinity sensing and immunosensing", Biosensors & Bioelectronics 6, 215–255 (1991), D. G. Hall, "Optical waveguide diffraction gratings: coupling between guided modes", in Progress in Optics XXIX, ed. E. Wolf, Elsevier, N.Y. (1991):

The penetration depth of the evanescent field of a planar waveguide into the superstrate is expressed by the equation $$\Delta z_{eva} = \lambda/2\pi \cdot \frac{1}{\sqrt{N_{eff}^2 - n_{super}^2}}$$

for the effective modal refractive index $N_{eff}$, the superstrate refractive index $n_{super}$, and for the working wavelength λ. In the above equation z denotes the coordinates vertical to the waveguide surface, x denotes the coordinates of the waveguide propagation. Taking into account the standardisation factor f for the electric field strength at the waveguide surface $$f = \frac{n_{film}^2 - N_{eff}^2}{n_{film}^2 - n_{sub}^2},$$

in which $n_{film}$ is the refractive index of the waveguide and $n_{sub}$ is the refractive index of the substrate, there is obtained an intensity curve $I_E$ of the evanescent field above the waveguide proportional to:

$$I_E \sim f \cdot e^{-2z/\Delta z_{eva}}.$$

This intensity curve of the exciting evanescent fields vertical to the waveguide surface determines the essential scaling factor for dimensioning the layer thickness and refractive index of the waveguide. For analytical utilities for the detection of luminescent molecules in the proximity of the waveguide layer, it is necessary to take into account the distance of the molecule from the waveguide surface when dimensioning the waveguide.

For luminescence detection it has now been found that the evanescent back coupling of luminescence is an efficient process for thin, highly refractive planar waveguides. The choice of layer thickness and refractive index has an effect on both the (computable) excitation efficiency as well as on the evanescent back coupling. In the latter case there is competition between the input-coupling of the radiation fractions of bound molecules in the proximity of the waveguide surface and the input-coupling of unbound molecules from the sample volume.

For an efficient detection of molecules having luminescent properties in the proximity of the waveguide surface by the process of this invention it has been found that the waveguide parameters must lie in the following range:

refractive index $n_{film} \geq 1.8$ for the excitation wavelength $\lambda$, layer thickness $t_{film} \leq$ for the excitation wavelength $\lambda$, preferably $t_{film} \leq \lambda/2$.

A particularly advantageous embodiment of the process is that when the layer thickness is selected in the range from 40 to 160 nm, and simultaneously the depth modulation of the gratings is from 3 to 60 nm, the ratio of depth modulation to layer thickness being <0.5.

These wavelengths can also be characterised in that they typically permit only the propagation of waveguide modes of low order $m \leq 3$.

The luminescence which is evanescently coupled back into the waveguide is transported therein; characteristic therefore is the attenuation coefficient $\Gamma$ of the guided wave. Given a low Stokes' shift, identical attenuation data for the excitation and luminescence radiation can be assumed (possible causes of the waveguide decay are scattering losses at the interfaces of the waveguide as well as absorption in the waveguide layer or in the substrate or superstrate. If there are no pronounced narrow absorption bands, then no significant change in decay caused by the Stokes' shift of typically 10–50 nm is to be expected both for scattering as well as for absorption. Such spectrally narrow-band absorption effects must be avoided in selecting the material for the sensor platform).

This luminescence radiation transported in the waveguide must be coupled out and guided to the detection system. An end-plane output-coupling is not expedient: on the one hand it requires a high quality of the wavelength edges and in some cases contacting the optical detection means via a liquid or gel immersion and, on the other hand, the integration of the sensor elements together with the fluid cell is thereby hindered.

The use of a second coupling grating, which is spatially separated from the coupling grating for the input-coupling of the excitation radiation, for coupling out the luminescence radiation is able to avoid completely the end-plane problem. A further advantage is that the grating distance A in direction x (i.e. in the direction of the guided wave) can be freely chosen. The possibility is thereby afforded of an optimum adjustment of the distance A to the attenuation for each wavelength without the necessity of altering the external dimensions of sensor and fluid cell. Furthermore, it is advantageous that the outside edges of the sensor element do not have to meet any optical quality requirements, so that their configuration can be adjusted to the fluid cell—in particular to the configuration of the sealing employed.

An optimum value for the grating distance B has been found to be $B = x_{1/e}$, with a variation possibility in the range of $B \approx (0.2-3)^* x_{1/e}$ ($x_{1/e}$: 1/e length for the drop in intensity of the guided excitation wave in direction x).

(Conversion.$\Gamma[dB/cm] \rightarrow x_{1/e}[1/mm]$:$x_{1/e}=100/(\ln 10^*\Gamma)$).

For greater distances, both excitation light as well as guided luminescence light is strongly attenuated and lead to a strong signal reduction. The downward limitation is not expressed primarily by excitation and back-coupling, but rather by the demands associated therewith made of the positioning of both gratings and of the excitation radiation on the input-coupling grating. Here spacings of less than 100 μm are inexpedient, also in view of the dimensioning of the width of the input-coupling grating described below and the light diameter of the excitation radiation on the edge of the input-coupling grating.

The invention is described hereinbelow in more detail by means of the figures.

Figure 1:
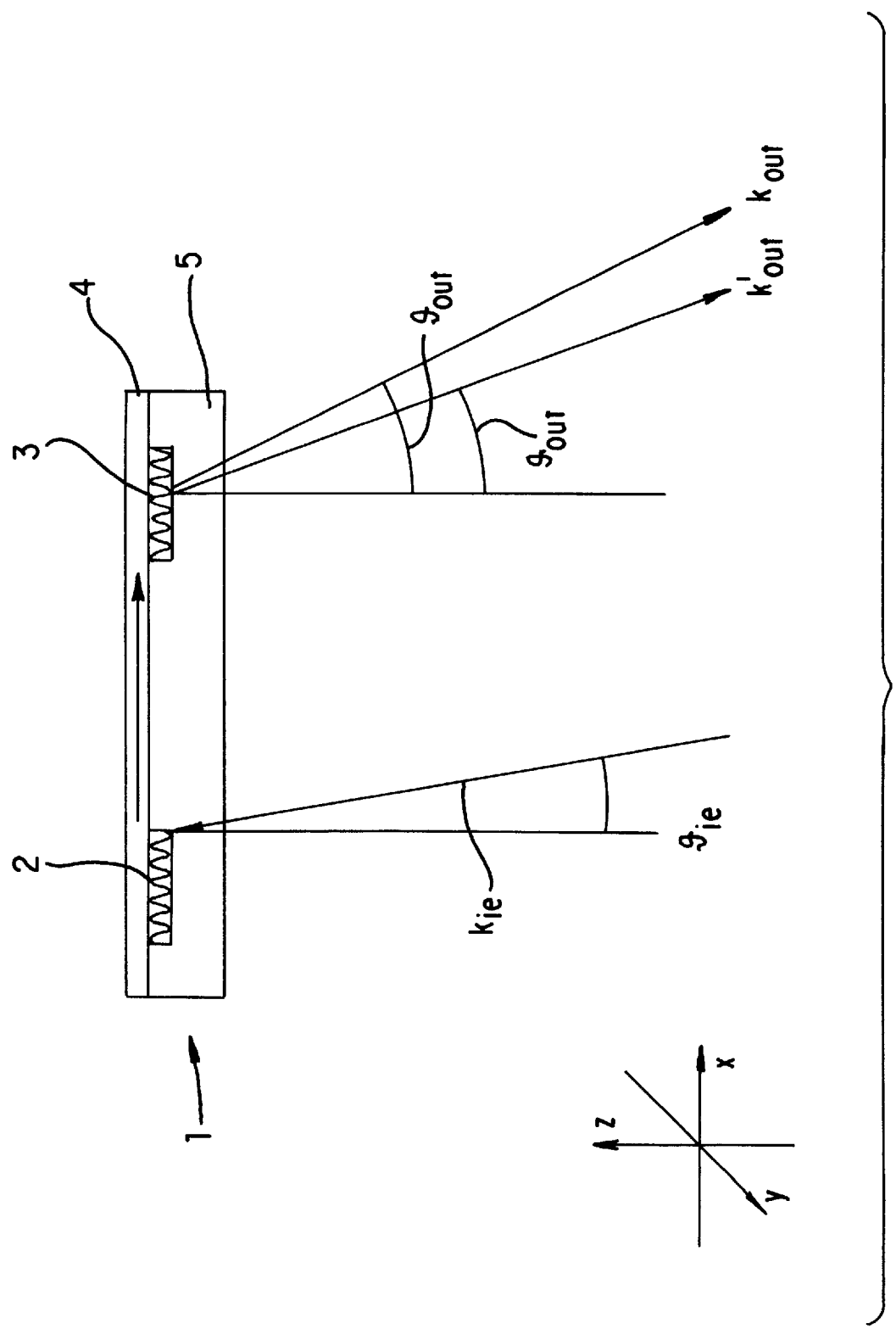
FIG. 1 shows a schematic sideview of an optical sensor platform which is particularly suitable for carrying out the inventive process with a possible radiation curve.

In FIG. 1, 1 is the sensor platform, 2 is the coupling grating for coupling in the excitation radiation, and 3 is that for coupling out the luminescence; 4 is the waveguiding layer and 5 is the substrate.

FIG. 1 shows a possible path of rays for the input- and output-coupling of excitation and luminescence radiation into and out of the sensor platform. A guided wave with propagation in direction x is excited by the coupling grating 2 in the sensor plane when the resonance condition in respect of the x components of the wave vectors is met:

$$k_{WL} = k_{ein} \pm m^* k_G = k_{ein} \pm m^* 2\pi/\Lambda_G,$$

m: integer, $k_G$: reciprocal grating vector $k_{WL} = 2\pi/\lambda * N_{eff} = k_O * N_{eff}$: wave vector-guided wave with effective modal refractive index $N_{eff}$ In FIG. 1, a negative angle $\theta$ is shown for the input-coupling with $k_{in} = k_0^* \cos \theta$ ($k_0$: magnitude of wave vector in the plane of the drawing) so that the guided wave runs in the "opposite direction" to the excitation (so-called "backward coupling"). Positive angles are chosen for coupling out the excitation wave (with $k_{out}$) and the the luminescence radiation (with $k_{out}$).

A high degree of background freedom is achieved by such an input- and output-coupling configuration with markedly different directions for reflected incident light and light which is coupled out. The spatial separation of the different radiation fractions ensures an optimum signal-to-noise ratio in luminescence detection: excitation radiation which is coupled out and luminescence radiation do not run in a common path of rays, so that filters (cut-off or bandpass filters, not shown in FIG. 1) are used only for suppressing scattered light, but not for the full intensity of the excitation radiation which is coupled out.

A further advantage of using an output-coupling grating is that different spectral components of the luminescence radiation are coupled out in different directions. It is therefore possible by means of this invention to detect also molecules in weakly luminescent sample media even without additional filters if the luminescence of molecules to be detected and of the sample medium is spectrally different.

The adjustment of the angles for input- and output-coupling is possible through the choice of grating constants $\Lambda_1$ and $\Lambda_2$. For the preferred case shown in FIG. 1 with a direction separation between input- and output-coupling, the grating constants must be chosen with marked differences.

Alternatively, identical grating constants can be used for the gratings 2 and 3 to simplify fabrication of the sensor. This may be important for as cost-effective a fabrication of the sensor as possible, as a number of process steps are omitted when using holographic structuring for grating fabrication. The spatial separation of the direction of excitation which is coupled out and luminescence radiation is still ensured when using identical grating constants. Only the safe separation of the direction of the reflected input-coupled radiation is omitted, so that additional measures for reflection screening are necessary, e.g. using apertures or light traps.

The coupling angles can be placed advantageously by the choice of the grating constants in the range from $|\theta| \approx 1°$ bis $50°$ (for the magnitude of the angle). Smaller values should be avoided on account of the Bragg reflection, as otherwise this reflection occurs even at low tolerances of the adjustment or of the levelness of the sensor, in conjunction with the non-occurrence of input- or output-coupling. Larger angles up to almost 90° are possible; but angles far beyond the normal ones for sensors should be avoided for a proper implementation of the path of rays.

The dimensioning of the grating depth can be in accordance with the prior art (T. Tamir, S. T. Peng "Analysis and Design of Grating Couplers", Appl. Phys. 14, 235–254 (1979); T. Tamir, "Beam and waveguide couplers" in "Integrated Optics", ed. T. Tamir, Springer, Berlin (1979). The so-called "leak parameter" $\alpha$ is used here as feature: $\alpha$ describes the 1/e decrease in intensity of a guided wave in a waveguide whose interface is provided with a coupling grating of depth $t_{grating}$. Hence $1/\alpha$ is the characteristic length for transferring the radiation energy from the guided wave to a wave that propagates freely or vice versa.

Important for the choice of the depth of the input-coupling grating is not primarily the absolute value of the leak parameter, but the adjustment of leak parameter and the radiation parameter of the incident light (beam diameter and divergence). For the optimum input-coupling of a laser beam with Gaussian profile (Gaussian parameter $w_0$) over a spatially limited grating it is necessary to observe the following conditions for leak parameters, beam diameter and positioning of the beam with respect to the grating edge:

$\alpha * w_0 = 1.36$
$x_0/w_0 = 0.733$.

The value $x_c$ describes the shift of the centre of the light spot towards the position of the grating edge. This shift must take place away from the edge to the structured area. By observing this condition it is possible to achieve input-coupling efficiencies of up to greater than 80%.

An analogous observation for the output-coupling leads to the result that here too a high coupling efficiency of 80% and more can be achieved. The premiss is that the lateral expansion of the grating in the direction x is markedly greater than the leak parameter. The intensity profile of the freely propagated beam of light which is coupled out is, however, inter alia, asymmetrical on account of the attenuation of the guided wave through the grating.

The following aspects shall be oberved when setting the leak parameter for the input-coupling
positioning the light spot with respect to the grating edge
miniaturising the sensor element.

Although small leak parameters ($\alpha \ll 1$/mm) and corresponding large beam diameters ($w_0 \gg 1$ mm) simplify positioning, the possibility of miniaturising the sensor is markedly restricted in the case of grating widths substantially greater than A=3 mm. The grating width should be A>3 *$w_0$ to effect complete coupling. In addition, inhomogeneities of the grating and the waveguide have a negative effect on the coupling efficiency. Whereas large leak parameters ($\alpha > 10$/mm) with beam diameters $w_0 < 10$ $\mu$m permit very small grating dimensions, they also permit a positioning accuracy of $\ll 100$ $\mu$m. Furthermore, the coupling efficiency is in this case limited by the fact that, inter alia, the beam divergence is markedly above the angular range of the coupling resonance.

We have found that the range of leak parameters $\alpha = (0.2-5)/1$ mm is a good compromise between adjustment requirements, positioning tolerances and miniaturisation. For the above described waveguide layer thicknesses, a range of $t_{grating} = 3-60$ nm, in particular of 3–40 nm, for the grating depth when using a sinusoidal modulation at the interface of substrate-waveguide typically corresponds to this range. As the leak parameter is heavily dependent on the profile form of the grating, the important dimension for the sensor function is not the geometrical depth but the leak parameter.

The substrate of the sensor platform must be transparent at the excitation and emission wavelength. The substrate may also be a plastics material as described e.g. in EP-A-0533074.

The substrate may also consist of a composite system of different materials, for example a layer system on a support plate or the like. In this case it is only necessary that the refractive index of the material directly adjacent to the waveguiding layer be smaller than the refractive index of the waveguiding layer.

A cost-effective fabrication of the sensor platform is possible in particular whenever microstructured polymers can be used as substrate for the waveguide coating. In this case the detection sensitivity can be limited by the excitation of the substrate-intrinsic luminescence. Excitation of this intrinsic luminescence and evanescent back-coupling occur at the waveguide-substrate material interface in similar manner to the above-described mechanisms at the waveguide-superstrate interface. This substrate-luminescence can be avoided by a non-luminescent interlayer of low refractive index (i.e. having a refractive index lower than or identical to that of the waveguide) which is applied to the substrate before the waveguide coating. A particularly suitable interlayer material is $SiO_2$ or consists essentially of $SiO_2$ having the composition $SiO_xH_yC_z$ into which lower hydrocarbon radicals may additionally be inserted. The thickness $t_{buffer}$ of this interlayer shall be chosen such that the energy transported by the evanescent field of the guided wave on the substrate side is localised within the interlayer. This condition is in practice met if $t_{buffer}$ is more than six times the value of the penetetration depth $z_{eva}$ of the evanescent field. A five-fold value is appropriate for an optimum signal-to-noise ratio in evanescent luminescence detection. This condition is safely met for $t_{buffer} \leq 2000$ nm.

A further advantage of the use of an interlayer may also be a reduction of the surface roughness of the substrate. The waveguide attenuation $\Gamma$ is thereby reduced with positive effects on the signal-to-noise ratio in evanescent luminescence detection.

Only essentially parallel light is suitable for luminescence excitation. Within the scope of this invention, the expression "essentially parallel" shall be understood as meaning a divergence of less than 5°. This means that light may be weakly divergent or weakly convergent. Greater divergences simplify the adjustment of the input-coupling angle, but reduce the luminescence signals, as the width of the input-coupling resonance is then markedly smaller than the divergence angle and thus only a small fraction of the impinging energy for the luminescence excitation is available.

Within the scope of this invention, a planar dielectric optical sensor platform means that said platform is in the form of a strip, a plate, a round disc or any other geometrical form, provided it can be seen by the naked eye to be planar. Deviations from planarity are not crucial if a guided wave is capable of propagation in the waveguiding layer and an input- and output-coupling scheme analogous to that in FIG. 1 can be realised. The chosen geometrical form can be governed by the construction of the entire apparatus into which the sensor platform is built. Preferred arrangements are those that permit substantial miniaturisation.

In addition to the above-described use of organic microstructured substrates it is also possible to use inorganic substrates such as glass or quartz. These have the advantage over polymers of low intrinsic luminescence. For the cost-effective fabrication of sensor platforms it is, however, expedient to provide these substrates with a coating of low refractive index into which the grating structure for the coupling gratings is inserted as described in EP-A-0533074.

Furthermore, the coupling gratings can be located at the waveguide/superstrate interface.

Methods of producing such gratings are known. Mainly photolithographic or holographic methods and etching techniques are used for their production, as described, inter alia, in Chemical, Biochemical and Environmental Fiber Sensors V. Proc. SPIE, Vol. 2068, 1–13, 1994.

The grating structure can be produced on the substrate and afterwards transferred to the waveguiding layer in which the grating structure is then imaged, or the grating is produced in the waveguiding layer itself.

The grating period can be 200 to 1000 nm, while the grating advantageously has only one periodicity, i.e. is monodiffractive.

Within the scope of this invention the term "sample" shall be taken to mean the entire solution to be assayed which may contain a substance to be detected—the analyte. The detection can be made in a single-step or multistep assay in the course of which the surface of the sensor platform is contacted with one or more solutions. At least one of the solutions employed can contain a substance having luminescence properties which can be detected in the practice of this invention.

If a substance having luminescence properties is already adsorbed on the waveguiding layer (b), then the sample may also be free from luminiscent components. The sample can contain further constituents, typically pH buffers, salts, acids, bases, surface-active substances, viscosity-influencing modifiers or dyes. In particular, a physiological saline solution can be used as solvent. If the luminescent constituent itself is liquid, then the addition of a solvent can be dispensed with. In this case the sample can contain up to 100% of component having luminescence properties.

The sample may further contain a biological medium, for example egg yolk, a body fluid or constituents thereof, in particular blood, serum, plasma or urine. Furthermore, the sample may consist of surface water, solutions of extracts of natural or synthetic media such as soil or parts of plants, bioprocess broths or synthesis broths.

The sample can either be undiluted or used additionally with a solvent.

Suitable solvents are water, aqueous buffer and protein solutions and organic solvents. Suitable organic solvents are alcohols, ketones, esters, and aliphatic hydrocarbons. It is preferred to use water, aqueous buffers or a mixture of water and a water-miscible organic solvent.

The sample can, however, also contain constituents that are insoluble in the solvent, for example pigment particles, dispersants, natural and synthetic oligomers or polymers. In this case the sample is in the form of an optically turbid dispersion or emulsion.

Suitable luminescent compounds are luminescent dyes having a luminescence in the wavelength range from 330 nm to 1000 nm, typically including rhodamines, fluorescein derivatives, coumarin derivatives, distyryl biphenyls, stilbene derivatives, phthalocyanines, naphthalocyanines, polypyridyl-ruthenium complexes such as tris(2,2'-bipyridyl)ruthenium chloride, tris(1,10-phenanthroline) ruthenium chloride, tris(4,7-diphenyl-1,10-phenanthroline) ruthenium chloride and polypyridyl-phenazine-ruthenium complexes, platinum-porphyrin complexes such as octaethyl-platinum-porphyrin, long-life europium and terbium complexes or cyanine dyes. Particularly suitable for analyses in blood or serum are dyes having absorption and emission wavelengths in the range from 600–900 nm.

Particularly suitable luminescent compounds are dyes such as fluorescein derivatives which contain functional groups with which they can be covalently bonded, for example fluorescein isothiocyanate.

Also very suitable are the functional fluorescent dyes available from Biological Detection Systems Inc., for example the mono- and bifunctional Cy5.5™ dyes also described, inter alia, in Clinical Chemistry 40 (9): 1819–1822, 1994.

The preferred luminescence is fluorescence. It is preferred to use coherent light for the excitation, as the resonance condition at the input-coupling grating can thereby be met with high efficiency. The laser light sources used therefor will be chosen according to the absorption wavelengths of the luminescent or fluorescent molecules.

Of particular importance in this connection are laser diodes or superluminescent diodes, as such light sources make possible a high miniataturisation of the detection system assigned to the sensor platform.

The luminescent dyes eligible for use may also be chemically bonded to polymers or to one of the binding partners in biochemical affinity systems, e.g. antibodies or antibody fragments, antigens, proteins, peptides, receptors or their ligands, hormones or hormone receptors, oligonucleotides, DNA strands and RNA strands, DNA or RNA analogs, binding proteins such as protein A and G, avidin or biotin, enzymes, enzyme cofactors or inhibitors, lectins or carbohydrates. The covalent luminescent labelling last mentioned is the preferred utility for reversible or irreversible (bio) chemical affinity assays. It is further possible to use luminescent-labelled steroids, lipids and chelators. Intercalating luminescent dyes are also of particular interest for hybridisation assays with DNA strands or oligonucleotides, especially if—like different ruthenium complexes—they exhibit enhanced luminescence in the intercalation. If these luminescent-labelled compounds are brought into contact with their affinity partners immobilised on the surface of the sensor platform, then the binding can be determined quantitatively from the measured intensity of luminescence. A quantitative determination of the analyte is also possible by measuring the change in luminescence when the sample interacts with the luminophores, for example in the form of luminescence quenching with oxygen or of luminescence enhancement by conformation modifications of proteins.

Suitable materials for the production of the waveguiding layer are typically inorganic materials, preferably inorganic metal oxides such as $TiO_2$, $ZnO$, $Nb_5O_5$, $Ta_2O_5$, $HfO_2$, or $ZrO_2$.

$Ta_2O_5$ and $TiO_2$ are preferred.

In the process of this invention the sample can be brought into contact with the waveguiding layer in the immobile state as well as guided continuously over it, and the cycle can be open or closed.

A specific embodiment of the process consists in immobilising the substances having luminescent properties used for detecting the analyte direct at the surface of the waveguiding layer (b). The substance having luminescent properties can be, for example, a luminophore which is bound to a protein and which can thereby be excited to luminescence in this manner at the surface of the waveguiding layer. If a partner having affinity for the protein is guided over this immobilised layer, then the luminescence can be modified and the amount of said partner can be determined in this manner. In particular, both partners of an affinity complex can also be labelled with luminophores so as to be able to effect the determination of concentrations from the energy transfer between the two, e.g. in the form of luminescence quenching.

Another preferred embodiment of the process for carrying out chemical or biochemical affinity assays consists in immobilising on the surface of the sensor platform a specific binding partner as chemical or biochemical detector substance for the analyte itself or for one of the binding partners. The assay can be a single-step or multistep assay in the course of which, in successive steps, one or more than one solution containing binding partners for the detector substances immobilised on the surface of the sensor platform is guided, the analyte becoming bound in one of the partial steps. The detection of the analyte is effected by binding luminescent-labelled participants in the affinity assay. The luminescent-labelled substances used may consist of one or more than one binding partner of the affinity assay, or also of an analog of the analyte provided with a luminophore. The sole criterion is that the presence of the analyte leads selectively to a luminescence signal or selectively to a change in the luminescence signal.

The immobilisation of the detector substances may typically be carried out by hydrophobic absorption or covalent bonding direct on the waveguide layer or after chemical modification of the surface, for example by silanisation or applying a polymer layer. In addition, a thin interlayer consisting e.g. of $SiO_2$ can be applied as adhesion-promoting layer direct to the waveguide layer to facilitate the immobilisation of the detector substances direct on the waveguide. The thickness of this interlayer should not exceed 50 nm, preferably 20 nm.

Suitable detector substances are typically antibodies for antigens, binding proteins such as protein A and G for immunoglobulins, receptors for ligands, oligonucleotides and single strands of RNA and DNA for their complementary strands, avidin for biotin, enzymes for enzyme substrates, enzyme cofactors or inhibitors, lectins for carbohydrates. Which of the respective affinity partners is immobilised on the surface of the sensor platform will depend on the architecture of the assay.

The assay itself can be a single-step complexing process, for example a competitive assay, or also a multistep process, for example a sandwich assay.

In the simplest case of the competitive assay, the sample which contains the analyte in unknown concentration as well as a known amount of a compound that is similar except for luminescent labelling is brought in to contact with the surface of the sensor platform, where the luminscent-labelled and unlabelled molecules compete for the binding sites at their immobilised detector substances. A maximum luminescence signal is achieved in this assay configuration when the sample contains no analyte. With increasing concentration of the substance to be detected, the luminescence signals under observation become lower.

In a competitive immunoassay it does not necessarily have to be the antibody which is immobilised: the antigen too can be immobilised on the surface of the sensor platform as detector substance. Usually it is immaterial which of the partners is immobilised in chemical or biochemical affinity assays. This is a basic advantage of luminescence-based assays over methods such as surface plasmon resonance or interferometry, which are based on the change in adsorbed mass in the evanescent field of the waveguiding layer.

Further, in the case of competitive assays the competition does not need to be limited to binding sites at the surface of the sensor platform. For example, a known amount of an antigen can also be immobilised on the surface of the sensor platform and then brought into contact with the sample which contains an unknown amount to be detected of the same antigen as analyte as well as luminescent-labelled antibodies. In this case the competition between antigens that are immobilised on the surface and present in solution takes place for binding of the antibodies.

The simplest case of a multistep assay is a sandwich immunoassay in which a primary antibody is immobilised on the surface of the sensor platform. The binding of the antigen to be detected and of the luminiscent-labelled secondary antibody used for carrying out the detection to a second epitope of the antigen can be effected either by successive contacting with the solution containing the antigen and a second solution containing the luminiscent-labelled antibody, or by combining these two solutions beforehand, so that, finally, the partial complex consisting of antigen and luminescent-labelled antibody is bound.

Affinity assays may also comprise further additional binding steps. For example, in the case of sandwich immunoassays proteinA, which specifically binds immunoglobulins which then act as primary antibodies in a subsequent sandwich assay, which is carried out as described above, at their so-called $F_c$ part, can be immobilised on the surface of the sensor platform in a first step.

There is a whole host of further types of affinity assays, typically using the known avidinbiotin affinity system.

Examples of types of affinity assays will be found in J. H. Rittenburg, Fundamentals of Immunoassay; in Development and Application of Immunoassay for Food Analysis, J. H. Rittenburg (Ed.), Elsevier, Essex 1990, or in P. Tijssen, Practice and Theory of Enzyme Immunoassays, R. H. Burdon, P. H. van Knippenberg (Eds), Elsevier, Amsterdam 1985.

It is furthermore possible to use the surface of the sensor platform not only for single use but also to regenerate it. Under suitable conditions, for example low pH, elevated temperature, using organic solvents or so-called chaotropic reagents (salts), it is possible to dissociate the affinity complexes selectively without substantial impairment of the binding capacity of the immobilised detector substances. The exact conditions are strongly dependent on the particular affinity system.

Another essential embodiment of the process consists on the one hand in limiting the production of the signal—in the case of back-coupling this also applies to signal detection—to the evanescent field of the waveguide and, on the other, in the reversibility of the affinity complex formation as equilibrium process. Using suitable rates of flow in a continuous flow system it is possible to monitor in real time the binding or desorption or dissociation of bound luminescent-labelled affinity partners in the evanescent field. The process is therefore suitable for kinetic studies for determining different association or dissociation constants or also for displacement assays.

The detection of evanescently excited luminescence can be made by known methods. Photodiodes, photocells, photomultipliers, CCD cameras and detector arrays, for example CCD cells, may suitably be used. The luminescence can be imaged with optical elements such as mirrors, prisms, lenses, Fresnel lenses and gradient index lenses thereon. To select the emission wavelength it is possible to use known elements such as filters, prisms, monochromatic filters, dichromatic mirrors and diffraction gratings.

One advantage of the process of this invention is that, besides the detection of luminescence, the absorption of the irradiated excitation light can also be determined. Compared with multimodal waveguides of optical fibre or planar construction, a substantially better signal-to-noise ratio is achieved in this case. The simultaneous measurement of luminescence and absorption makes it possible to determine luminescence quenching effects with high sensitivity.

In a simple embodiment of the invention, the process can be carried out by irradiating with excitation light in continuous wave (cw) mode, i.e. excitation is effected with light intensity that is constant in time.

The process can, however, also be carried out by irradiation with excitation light in the form of a timed pulse with a pulse length of e.g. one picosecond up to 100 seconds, and by time-resolved detection of the luminescence—in the case of short pulse lengths—or at intervals of seconds to minutes. This method is particularly advantageous whenever it is desired e.g. to monitor the rate of a bond formation analytically or to prevent a decrease in the luminescence signal because of photochemical fading using short exposure times. By using appropriate short pulse length and suitable time-resolution of the detection it is further possible to distinguish scattered light, Raman emission and short-lived luminescence of any unwanted luminescent constituents of the sample and the sensor material from a luminescence of the labelling molecule, which is in this case preferably long-lived, by detecting the emission of the analyte only after this short-lived radiation has decayed. Moreover, time-resolved luminescence detection permits after pulsed excitation—just like modulated excitation and detection—investigation of the influence of the binding of the analyte on the decay of molecular luminescence. In addition to the specific recognition of the analyte by the immobilised detector substances and the spatial limitation of the signal production to the evanescent field of the waveguide, the molecular luminescence decay time can be utilised as a further criterion of selectivity.

The process can also be carried out by input-coupling the excitation light at one or more than one frequency with modulated intensity, and detecting the resultant phase shift and modulation of the sample luminescence.

The invention further relates to the use of the inventive process for the quantitative determination of analytes in chemical or biochemical affinity assays with known affinity partners and assay architectures by detecting the emission of labelled binding partners capable of luminescence, or by detecting changes in the luminescence properties of immobilised luminescent-labelled affinity partners by interaction with the analyte.

As signal production and detection are limited to the chemical or biochemical detection surface on the waveguide, and interference signals from the medium are discriminated, the binding of substances to the immobilised detector elements can be monitored in real time. It is therefore also possible to use the inventive process for affinity screening or for displacement assays, especially for pharmaceutical product development, by direct detection of association and dissociation rates in continuous flow systems with suitable flow rates.

In another of its aspects, the invention relates to the use of the inventive process for the quantitative determination of antibodies or antigens.

Yet another utility of the inventive process is for the quantitative determination of receptors or ligands, oligonucleotides, strands of DNA or RNA, DNA or RNA analogs, enzymes, enzyme substrates, enzyme cofactors or inhibitors, lectins and carbohydrates.

In a further aspect, the invention relates to the use of the inventive process for the selective quantitive determination of luminescent constituents in optically turbid fluids.

Optically turbid fluids may typically be biological fluids such as egg yolk, body fluids such as blood, serum or plasma, and also samples emanating from environmental analysis, including surface water, dissolved soil extracts and dissolved plant extracts. Suitable fluids are also the reaction solutions obtained in chemical production, in particular dye solutions or reaction solutions originating from the production of fluorescent whitening agents. Also suitable are all types of the dispersions and formulations typically used in the textile industry, provided these contain one or more than one luminescent component. The process can thus also be used for quality safeguarding.

The invention is illustrated in more detail by the following Example. The concentration M denotes mol per liter.

EXAMPLE

Optical system

The light source employed is a laser diode at $\lambda=670$ nm (Oz Optics). The adjustment to a light spot having a diameter in the sensor plane of 0.4 nm vertically to the lines of the coupling grating and 2.5 mm parallel to the grating lines is made by means of an imaging system.

The adjustment of the input-coupling angle and the positioning of the light spot with respect to the grating edge is carried out by means of mechanical adjustment units. The laser power on the sensor chip may be chosen in the range P=0 . . . 3 mW; while P=1.2 is chosen for the following experiments for the characterisation of of the gratings, and P=0.2 mW for the fluorescence measurements. Linear polarised light with TE or TM orientation can be input-coupled using rotatable polarising elements.

A flow cell sealed against the sensor by O rings is mounted on the topside of the sensor platform. The sample volume of the cell is c.8 $\mu$l. Different solutions can be introduced into the cell using jet pumps and reversing valves.

Excitation and detection are carried out as shown schematically in FIG. 1 from the underside of the sensor platform.

3 measurement channels are available for the detection, for the fluorescent and excitation light coupled out at the output-coupling grating (in the direction of $k'_{out}$ and $k_{out}$ according to FIG. 1), as well as, via a beam splitter, the incident excitation light (not shown in FIG. 1).

A multiplier in the single photon counting mode (Hamamatsu R 4632 SEL) with impulse-forming electronics (Hamamatsu C3 866) is used as detector for the fluorescence radiation. Its TTL output signal is counted by a conventional impulse counter (Hewlett-Packard 53131 A). The fluorescence radiation for the angle sectors can be focused on the detector via a focusing lens system. Interference filters for suppressing scattered light (band-pass at $\lambda=725$ nm with half-width 25 nm, Omega) are positioned in front of the detector.

Si diodes (UDT PIN 10D) with a measurement amplifier (UDU 101 C) connected in series are used as reference detectors for incident and excitation radiation which is coupled out.

All 3 measurement channels can be evaluated simultaneously while carrying out the assay described below using a conventional data input system.

Sensor platform

Polycarbonate which is microstructured in the following manner with two gratings for input- and output-coupling is used as substrate:

Input-coupling grating with period $\Lambda_1=(299.5\pm0.7$ nm), depth $t_1=6.9$ nm to 12.3 nm, output-coupling grating with $\Lambda_2=(489.5\pm0.6$ nm), depth $t_1=8.2$ nm to 12.8 nm, both gratings having approximately $\sin^4$ profile.

Figure 2:
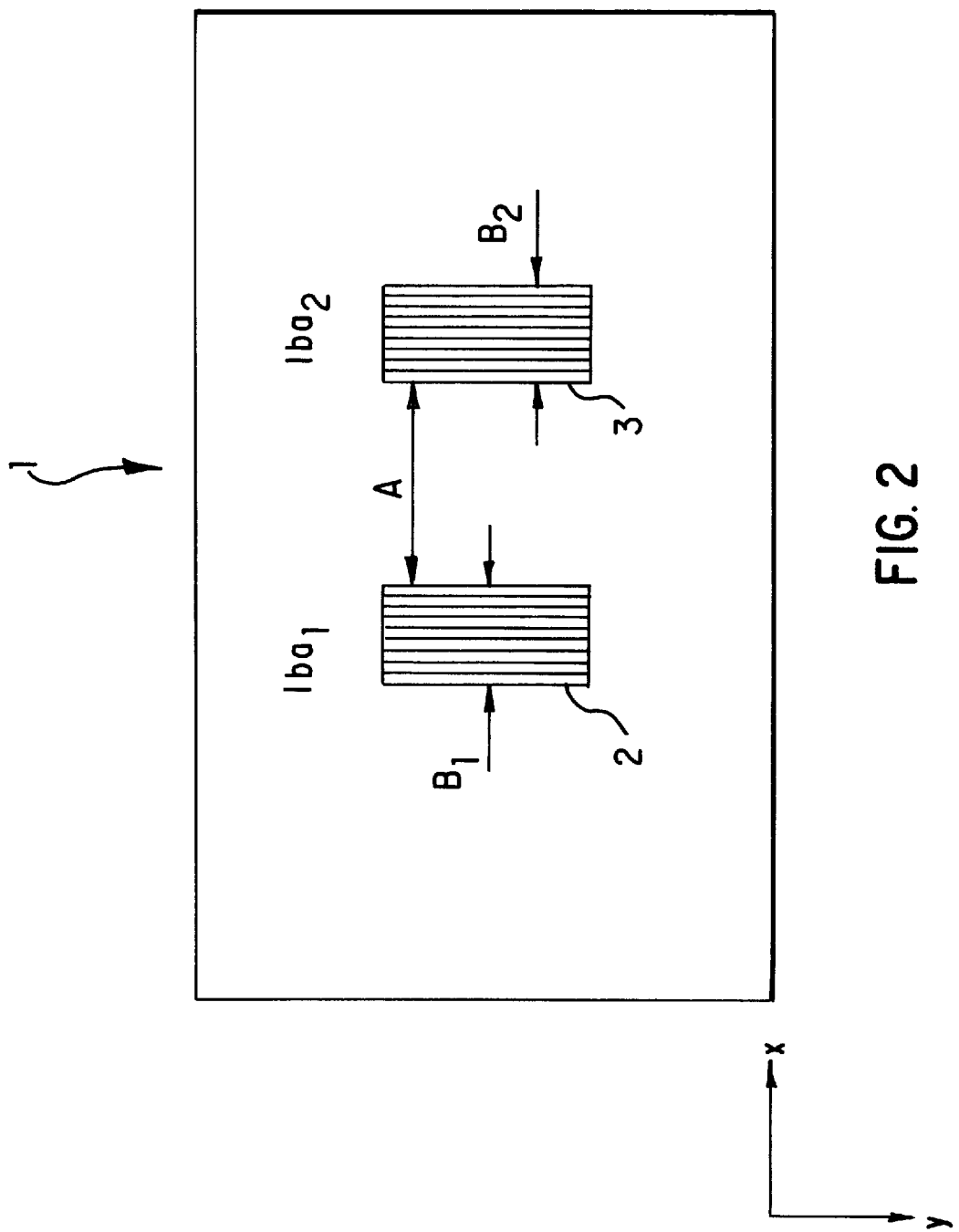
FIG. 2 shows a top view of the sensor platform of FIG. 1.

The arrangement of the gratings on the sensor is in accordance with FIG. 2, with the following geometrical values: grating distance A=4 mm, grating width (vertically to lines) $B_1=B_2=2$ mm, grating height (parallel to lines) 4 mm, the dimensions of the sensor platform being 12×20 mm².

To suppress self-fluorescence of the polycarbonate, this substrate is coated with a $SiO_2$ interlayer having a refractive index n=1.46 and a thickness of $t_{buffer}$=(100±10 nm), therafter the waveguiding layer of $TiO_2$ of high refractive index $n_{film}$ 2.35 at λ=670 nm and of layer thickness $t_{film}$= (170±5 nm).

By means of the excitation light the modes with order m=0 can be excited in the waveguide for this grating-waveguide combination.: for $TE_0$ the input-coupling is effected under an angle of Θ=(-10±1.6)°, alternatively for $TM_0$ under the angle Θ=(-22.7±3.7)°.

The fluorescence radiation is coupled out with TE polarisation in an angular range of Θ=31°. . . 40°, the excitation light at angles of Θ>42°. A spectral region of λc.685 nm . . . 715 nm. For TM polarisation the output-coupling angle is in the range Θ=17°. . . 25° for the fluorescence and Θ>27° for the excitation radiation. For TE polarisation a light efficiency of P=30 . . . 50 μW is detected for an incident laser intensity of P=1.2 mW after the output-coupling grating.

Detection of Cy5.5™-labelled immunoglobulin

Labelling of immunoglobulin with Cy 5.5™ dye:

Rabbit immunoglobulin (rabbit IgG, Sigma Chemicals) was labelled in the same way as described by the dye manufacturer with bifunctional cyanine dye FluoroLink™ Cy 5.5™ (Biological Detection Systems, Pittsburgh, Pa. 15238, USA):

1. Solution of 2.5 mg of rabbit IgG in 1 ml of dye, incubation for 45 min, solution shaken every 10 min.
2. Addition of this solution to 1 ml of dye, incubation for 45 min, solution shaken every 10 min.
3. Separation of protein-bonded and unbonded dye over a Sephadex R G25 column (Pharmacia LKB, Biotechnology AB, Uppsala, Sweden), which has previously been equilibrised with 50 ml of phosphate buffer at pH 7:
   discarding the 1 ml
   collecting a number of fractions
4. Determining the dye/protein ratio from the optical densities at 678 nm (absorption band of the dye) and at 280 nm (protein absorption band). A ratio of 1 dye molecule to 2 protein molecules was determined therefrom.

Solution used
1) Buffer solution consisting of (0.041M of $Na_2HPO_4$+ 0.028M of $KH_2PO_4$), 0.151M of NaCl, 200 mg/l of sodium azide, 50 ml of methanol, bulked to 1 liter with distilled water;
2) solution for immobilising protein A (Sigma Chemicals): 1 mg/ml of dist. water;
3) neutralisation solution: buffer solution 1)+10 mg/ml of bovine serum albumin (BSA, Sigma Chemicals);
4) rinsing solution: is also used for determining the background signal, buffer solution 1)+1 mg/ml of BSA;
5) sample solutions: Cy 5.5™-labelled immunoglobulin in different concentrations $10^{-8}$M $10^{-9}$M; $3·10^{-10}$M, $1·10^{-10}$M in buffer solution 1 with 1 mg/ml of BSA;
6) regeneration solution: glycine buffer, pH 2.5

Applying the biochemical indicator layer of protein A

The optical sensor platform is incubated for 10 hours with solution 2) to immobilise protein A. To neutralise any still free adsorption sites, the sensor platform is washed with distilled water and then incubated again for 1 hour in the neutralisation solution which contains 10 g/l of BSA.

Measuring procedure/assay

During the entire procedure, a flow of 0.25 ml/min is maintained over the active sensor surface:

The process consists of the following individual steps:
washing for 4 minutes with rinsing solution 4), recording of background signal;
addition of sample solution 5) over 4 minutes;
washing for 4 minutes with rinsing solution 4).
addition of regeneration solution 6) over 4 minutes
washing for 4 minutes with rinsing solution 4).

The fluorescence signal coupled out via the second grating is measured over the entire process. At the different concentrations, the following changes of signal are recorded at the end of the addition of sample, compared with the initial background signal (signal/noise ratio between 50 and 100 impulses per second (cps):

| [Cy 5.5-tgG] | fluorescence signal [cps] |
| --- | --- |
| $10^{-8}$M | 7000 |
| $10^{-9}$M | 850 |
| $3·10^{-10}$M | 300 |

The detection limit for the detection of fluorescence by grating output-coupling is clearly below $3·10^{-10}$M, corresponding to an analyte concentration of $3·10^{-13}$ mol of Cy5.5-labelled IgG.

What is claimed is:

1. A process for determining luminescence with a planar dielectric optical sensor platform which consists of a transparent substrate (a) to which a thin transparent waveguiding layer (b) is applied, which sensor platform is provided with a coupling first grating having a depth modulation of from 3 to 60 nm for the input-coupling of the excitation light and the refractive index of said substrate (a) is lower than the refractive index of the waveguiding layer (b), by bringing a liquid sample as superstrate into contact with the layer (b), and measuring the luminescence produced by substances having luminescence properties in the sample, or by substances having luminescence properties immobilised on the layer (b), optoelectronically, by coupling the excitation light with the coupling grating into the planar waveguide so that it traverses the waveguiding layer, whereby the substances having luminescence properties are excited to luminescence in the evanescent field of the waveguiding layer, which process comprises using a waveguiding layer having a thickness smaller than the wavelength λ of the excitation radiation and which consists of a material whose refractive index at the wavelength of the excitation radiation is ≧1.8, and coupling out from the waveguiding layer, and detecting, the luminescence radiation coupled back into the waveguiding layer (b) with a second coupling grating spatially separated from the first coupling grating.

2. A process according to claim 1, which comprises using a waveguiding layer having a thickness smaller than λ/2.

3. A process according to claim 1, wherein the thickness of the waveguiding layer is 40 to 160 nm.

4. A process according to claim 1, wherein the excitation radiation is coupled out under an angle different from that of the luminescence radiation.

5. A process according to claim 1, wherein the excitation radiation is coupled into the waveguide in reverse direction and both the excitation light transmitted by the waveguide and the luminescence transported in the waveguide is coupled out in forward direction.

6. A process according to claim 1, wherein the excitation radiation is coupled into the waveguide under an angle in the range from ≈1° to -50°.

7. A process according to claim 1, wherein the luminescence radiation coupled back into the waveguide is coupled out under an angle in the range from ≈1° to 50°.

8. A process according to claim 1, wherein the luminescence of the substrate is suppressed.

9. A process according to claim 1, wherein essentially parallel light is used for exciting luminescence.

10. A process according to claim 1, wherein the substances capable of luminescence used for detecting the analyte are immobilised direct on the surface of the waveguiding layer.

11. A process according to claim 1, which comprises immobilising a specific binding partner as chemical or biochemical detector substance for the analyte itself or for one of the binding partners on the surface of the sensor platform in a multi-step assay in the course of which the analyte becomes bound in one of the partial steps.

12. A process according to claim 1, wherein the absorption of the irradiated excitation light is simultaneously determined.

13. A process according to claim 1, wherein the excitation light is coupled into the waveguide in continuous wave (cw) mode.

14. A process according to claim 1, which comprises input-coupling the excitation light in the form of a timed pulse and detecting the luminescence time-resolved.

15. A process according to claim 14, wherein the pulse length is adjusted from one picosecond up to 100 seconds.

16. A process according to claim 1, which comprises input-coupling the excitation light with modulated intensity at one or more than one frequency, and detecting the resultant phase shift and modulation of the sample luminescence.

17. A process according to claim 1, wherein the sample to be detected is egg yolk, blood, serum, plasma or urine.

18. A process according to claim 1, wherein the sample to be detected is a surface water, a soil or plant extract, a bioprocess broth or synthesis broth.

19. Use of a process according to claim 1, for the quantitative determination of biochemical substances in affinity sensing.

20. Use of a process according to claim 1, for the quantitative determination of antibodies or antigens.

21. Use of a process according to claim 1, for the quantitative determination of receptors or ligands, oligonucleotides, DNA or RNA strands, DNA or RNA analogs, enzymes, enzyme substrates, enzyme cofactors or inhibitors, lectins and carbohydrates.

22. Use of a process according to claim 1, for the selective quantitative determination of luminescent components in optically turbid fluids.

23. An optical sensor platform (1) for determining luminescence radiation, comprising essentially a planar optically transparent substrate (5) to which is applied a thin waveguiding layer (4), said sensor platform (1) being provided with a first coupling grating having a depth modulation of from 3 to 60 nm (2) for the input-coupling of excitation radiation and the refractive index of the substrate is smaller than the refractive index of the waveguiding layer (4), wherein the thickness of said waveguiding layer (4) is smaller than the wavelength $\lambda$ of the excitation radiation, and said waveguiding layer (4) consists of a material whose refractive index at the wavelength of the excitation light is >1.8, and the sensor platform (1) comprises a second coupling grating (3) which is spatially separated from the first coupling grating (2) for coupling out the luminescence radiation coupled back into the waveguiding layer.

24. A sensor platform according to claim 23, wherein the thickness of the waveguiding layer (4) is smaller than $\lambda/2$.

25. A sensor platform according to claim 23, wherein the thickness of the waveguiding layer (4) is 40 to 160 nm.

26. A sensor platform according to claim 23, wherein the grating constant of the first coupling grating (2) for the input-coupling of excitation radiation is different from the grating constant of the second coupling grating (3) for coupling out the luminescence radiation.

27. A sensor platform according to claim 23, wherein the grating distance is $B \leq X_{1/e}$, where $X_{1/e}$ is the length within which the intensity $l_0$ of the incident radiation has fallen to $l_0/e$.

28. A sensor platform according to claim 27, wherein the grating distance is $B \geq 0.2 \cdot X_{1/e}$.

29. A sensor platform according to claim 1, wherein an interlayer of low refractive index for suppressing the luminescence of the substrate is provided between substrate (5) and waveguiding layer (4).

30. A sensor platform according to claim 29, wherein the interlayer of low refractive index consists essentially of $SiO_2$ or $SiO_xC_yH_z$.

31. A sensor platform according to claim 29, wherein the thickness of the interlayer is $\leq 1000$ nm.

32. A sensor platform according to claim 23, wherein an organic microstructured substrate is used.

33. A sensor platform according to claim 23, wherein an organic substrate with a microstructured organic coating is used.

34. A sensor platform according to claim 23, wherein the planar transparent waveguiding layer (4) consists of $Ta_2O_5$ oder $TiO_2$.

35. A sensor platform according to claim 23, wherein an adhesion promoting layer is present between the waveguiding layer (4) and the sample.

36. A sensor platform according to claim 35, wherein the adhesion promoting layer has a thickness of $\leq 50$ nm.

* * * * *